(12) United States Patent
Zimmerman et al.

(10) Patent No.: US 6,572,860 B1
(45) Date of Patent: Jun. 3, 2003

(54) IMMUNOGENIC CONJUGATED POLYPEPTIDE FOR TREATMENT OF HERPES SIMPLEX VIRUS

(75) Inventors: Daniel H. Zimmerman, Bethesda, MD (US); Kenneth S. Rosenthal, Akron, OH (US)

(73) Assignee: CEL-SCI Corporation, Vienna, VA (US)

( * ) Notice: Subject to any disclaimer, the term of this patent is extended or adjusted under 35 U.S.C. 154(b) by 0 days.

(21) Appl. No.: 09/509,593

(22) PCT Filed: Sep. 29, 1998

(86) PCT No.: PCT/US98/20681

§ 371 (c)(1),
(2), (4) Date: Mar. 30, 2000

(87) PCT Pub. No.: WO99/16710

PCT Pub. Date: Apr. 8, 1999

Related U.S. Application Data

(60) Provisional application No. 60/060,422, filed on Sep. 30, 1997.

(51) Int. Cl.[7] ............................................. A61K 39/385
(52) U.S. Cl. ................. 424/194.1; 424/185.1; 424/192.1; 424/193.1; 424/196.11; 424/202.1; 424/204.1; 424/231.1; 530/403
(58) Field of Search ........................... 424/184.1, 185.1, 424/192.1, 198.1, 204.1, 231.1, 196.11, 193.1, 194.1, 202.1; 530/403, 300

(56) References Cited

U.S. PATENT DOCUMENTS 5,652,342 A    7/1997    Zimmerman et al.

OTHER PUBLICATIONS

"Differences in the Recognition . . . ", Nugent et al. Cellular Immunology 165, 55–64 (1995).

Hinuma, S., et al, Fed. of Eur. Biochem, Soc., Aug. 1991, vol. 288, No. 1–2, p. 138–142.

Nakao, M. et al, J. Infect. Dis., 1994, vol. 169, pp. 787–791.

Banks, T. et al, J. of Virology, 1993, vol. 67, No. 1, pp. 613–616.

Nencioni, L. et al, J. of Immunol., Aug. 1, 1987, vol. 139, No. 3, pp. 800–804.

Cammarota, G. et al, Nature Apr. 30, 1992, vol. 356, pp. 799–801.

Zimmerman, D. et al, Vacc. Res. 1996, vol. 5, pp. 103–118.

Primary Examiner—Laurie Scheiner
(74) Attorney, Agent, or Firm—Sherman & Shalloway

(57) ABSTRACT

Peptide constructs chemically synthesized to contain a Herpes Simplex Virus specific antigenic peptide, such as, the 322–332 peptide (H1) from the ICP27 protein of Herpes Simplex Virus (HSV-1) and a peptide from a T cell binding ligand (TCBL), such as β-2M (aa 35–50), which elicits a TH1-like response in vitro tests in mice, were protective against challenge with HSV.

8 Claims, 7 Drawing Sheets

SEQUENCE LISTING (1) GENERAL INFORMATION:

(iii) NUMBER OF SEQUENCES:21

(2) INFORMATION FOR SEQ ID NO: 1:

(i) SEQUENCE CHARACTERISTICS:
      (A) LENGTH:11 amino acids
      (B) TYPE:amino acids
      (C) TOPOLOGY:linear (ii) MOLECULE TYPE:

(iii) HYPOTHETICAL:

(v) FRAGMENT TYPE:internal (vi) ORIGINAL SOURCE:
      (A) ORGANISM:HSV1

(ix) FEATURE:
      (A) NAME/KEY:Peptide H1 of ICP27

```
            (B) LOCATION:322 to 332
            (C) IDENTIFICATION METHOD:
            (D) OTHER INFORMATION:

(xi) SEQUENCE DESCRIPTION:SEQ ID NO:1:

Leu Tyr Arg Thr Phe Ala Gly Asn Pro Arg Ala
5                   10

(2) INFORMATION FOR SEQ ID NO: 2:

(i) SEQUENCE CHARACTERISTICS:
            (A) LENGTH:12 amino acids
            (B) TYPE:amino acids
            (C) TOPOLOGY:linear (ii) MOLECULE TYPE:

(iii) HYPOTHETICAL:

(v) FRAGMENT TYPE:internal (vi) ORIGINAL SOURCE:HSV1
            (A) ORGANISM:

(ix) FEATURE:
            (A) NAME/KEY:Peptide H2 of ICP27
            (B) LOCATION:
            (C) IDENTIFICATION METHOD:

(xi) SEQUENCE DESCRIPTION:SEQ ID NO: 2:

Ala Glu Ile Asp Tyr Ala Thr Leu Gly Val Gly Val
5                   10

(2) INFORMATION FOR SEQ ID NO: 3:

(i) SEQUENCE CHARACTERISTICS:
            (A) LENGTH:9 amino acids
            (B) TYPE:amino acids
            (C) TOPOLOGY:linear (ii) MOLECULE TYPE:

(iii) HYPOTHETICAL:

(v) FRAGMENT TYPE:internal (vi) ORIGINAL SOURCE:
            (A) ORGANISM:HSV1

(ix) FEATURE:
            (A) NAME/KEY:ICP27
            (B) LOCATION:448 to 456
            (C) IDENTIFICATION METHOD:
            (D) OTHER INFORMATION:

(xi) SEQUENCE DESCRIPTION:SEQ ID NO:3:

Asp Tyr Ala Thr Leu Gly Val Gly Val
5

(2) INFORMATION FOR SEQ ID NO: 4:

(i) SEQUENCE CHARACTERISTICS:
            (A) LENGTH:8 amino acids
            (B) TYPE:amino acids
            (C) TOPOLOGY:linear (ii) MOLECULE TYPE:

(iii) HYPOTHETICAL:

(v) FRAGMENT TYPE:internal (vi) ORIGINAL SOURCE:HSV1
```

```
            (A) ORGANISM:

(ix) FEATURE:
           (A) NAME/KEY:Peptide B1 of glycoprotein B
           (B) LOCATION:498 to 505
           (C) IDENTIFICATION METHOD:

(xi) SEQUENCE DESCRIPTION:SEQ ID NO: 4:

Ser Ser Ile Glu Phe Ala Arg Leu
5

(2) INFORMATION FOR SEQ ID NO: 5:

(i) SEQUENCE CHARACTERISTICS:
           (A) LENGTH:12 amino acids
           (B) TYPE:amino acids
           (C) TOPOLOGY:linear (ii) MOLECULE TYPE:

(iii) HYPOTHETICAL:

(v) FRAGMENT TYPE:internal (vi) ORIGINAL SOURCE:
           (A) ORGANISM:HSV1

(ix) FEATURE:
           (A) NAME/KEY:glycoprotein C
           (B) LOCATION:128 to 139
           (C) IDENTIFICATION METHOD:
           (D) OTHER INFORMATION:

(xi) SEQUENCE DESCRIPTION:SEQ ID NO:5:

Asp Arg Arg Asp Pro Leu Ala Arg Tyr Gly Ser Arg
5                   10

(2) INFORMATION FOR SEQ ID NO: 6:

(i) SEQUENCE CHARACTERISTICS:
           (A) LENGTH:30 amino acids
           (B) TYPE:amino acids
           (C) TOPOLOGY:linear (ii) MOLECULE TYPE:

(iii) HYPOTHETICAL:

(v) FRAGMENT TYPE:internal (vi) ORIGINAL SOURCE:
           (A) ORGANISM:HSV1

(ix) FEATURE:
           (A) NAME/KEY:glycoprotein D
           (B) LOCATION:
           (C) IDENTIFICATION METHOD:

(xi) SEQUENCE DESCRIPTION:SEQ ID NO: 6:

Lys Arg Ala Leu Ala Asp Ala Ser Leu Lys Met Ala Asp Pro Asn Arg
5                   10                  15

Phe Arg Gly Lys Asp Leu Pro Val Leu Asp Glu Leu Asp Thr
20                  25

(2) INFORMATION FOR SEQ ID NO: 7:

(i) SEQUENCE CHARACTERISTICS:
           (A) LENGTH:13 amino acids
           (B) TYPE:amino acids
           (C) TOPOLOGY:linear (ii) MOLECULE TYPE:
```

```
        (iii) HYPOTHETICAL:

(v) FRAGMENT TYPE:internal (vi) ORIGINAL SOURCE:
             (A) ORGANISM:HSV1

(ix) FEATURE:
             (A) NAME/KEY:glycoprotein D
             (B) LOCATION:
             (C) IDENTIFICATION METHOD:
             (D) OTHER INFORMATION:

(xi) SEQUENCE DESCRIPTION:SEQ ID NO:7:

Leu Lys Met Ala Asp Pro Asn Arg Phe Arg Gly Lys Asp
5                   10

(2) INFORMATION FOR SEQ ID NO: 8:

(i) SEQUENCE CHARACTERISTICS:
             (A) LENGTH:17 amino acids
             (B) TYPE:amino acids
             (C) TOPOLOGY:linear (ii) MOLECULE TYPE:

(iii) HYPOTHETICAL:

(v) FRAGMENT TYPE:internal (vi) ORIGINAL SOURCE:
             (A) ORGANISM:HSV1

(ix) FEATURE:
             (A) NAME/KEY:glycoprotein D
             (B) LOCATION:
             (C) IDENTIFICATION METHOD:

(xi) SEQUENCE DESCRIPTION:SEQ ID NO: 8:

Ser Leu Lys Met Ala Asp Pro Arg Asn Arg Phe Arg Gly Lys Asp Leu
5                   10                  15

Pro (2) INFORMATION FOR SEQ ID NO: 9:

(i) SEQUENCE CHARACTERISTICS:
             (A) LENGTH:15 amino acids
             (B) TYPE:amino acids
             (C) TOPOLOGY:linear (ii) MOLECULE TYPE:

(iii) HYPOTHETICAL:

(v) FRAGMENT TYPE:internal (vi) ORIGINAL SOURCE:
             (A) ORGANISM:

(ix) FEATURE:
             (A) NAME/KEY:a-2 microglobulin, Peptide J
             (B) LOCATION:35 to 47
             (C) IDENTIFICATION METHOD:
             (D) OTHER INFORMATION:

(xi) SEQUENCE DESCRIPTION:SEQ ID NO:9:

Asp Leu Leu Lys Asn Gly Glu Arg Ile Gly Lys Val Glu Gly Gly
5                   10                  15

(2) INFORMATION FOR SEQ ID NO: 10:

(i) SEQUENCE CHARACTERISTICS:
```

(A) LENGTH:27 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:

(xi) SEQUENCE DESCRIPTION:SEQ ID NO: 10:

Asp Leu Leu Lys Asn Gly Glu Arg Ile Glu Lys Val Glu Gly Gly Gly
5               10              15

Leu Tyr Arg Thr Phe Ala Gly Asn Pro Arg Ala
20              25

(2) INFORMATION FOR SEQ ID NO: 11:

(i) SEQUENCE CHARACTERISTICS:
        (A) LENGTH:28 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:11:

Asp Leu Leu Lys Asn Gly Glu Arg Ile Glu Lys Val Glu Gly Gly Gly
5               10              15

Ala Glu Ile Asp Tyr Ala Thr Leu Gly Val Gly Val
20              25

(2) INFORMATION FOR SEQ ID NO: 12:

(i) SEQUENCE CHARACTERISTICS:
        (A) LENGTH:29 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:

(xi) SEQUENCE DESCRIPTION:SEQ ID NO: 12:

Asn Gly Gln Glu Glu Lys Ala Gly Val Val Ser Thr Gly Leu Ile Gly
5               10              15

Gly Gly Leu Tyr Arg Thr Phe Ala Gly Asn Pro Arg Ala

```
20              25

(2) INFORMATION FOR SEQ ID NO: 13:

(i) SEQUENCE CHARACTERISTICS:
        (A) LENGTH:26 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:13:

Leu His Gly Pro Glu Ile Leu Asp Val Pro Ser Thr Gly Gly Gly Leu
5               10              15

Tyr Arg Thr Phe Ala Gly Asn Pro Arg Ala
20              25

(2) INFORMATION FOR SEQ ID NO: 14:

(i) SEQUENCE CHARACTERISTICS:
        (A) LENGTH:27 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:

(xi) SEQUENCE DESCRIPTION:SEQ ID NO: 14:

Leu His Gly Pro Glu Ile Leu Asp Val Pro Ser Thr Gly Gly Gly Ala
5               10              15

Glu Ile Asp Tyr Ala Thr Leu Gly Val Gly Ala
20              25

(2) INFORMATION FOR SEQ ID NO: 15:

(i) SEQUENCE CHARACTERISTICS:
        (A) LENGTH:30 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:
        (D) OTHER INFORMATION:
```

(xi) SEQUENCE DESCRIPTION:SEQ ID NO:15:

Asn Gly Gln Glu Glu Lys Ala Gly Val Val Ser Thr Gly Leu Ile Gly
5               10                  15

Gly Gly Ala Glu Ile Asp Tyr Ala Thr Leu Gly Val Gly Tyr
20                  25                  30

(2) INFORMATION FOR SEQ ID NO: 16:

(i) SEQUENCE CHARACTERISTICS:
        (A) LENGTH:27 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:

(xi) SEQUENCE DESCRIPTION:SEQ ID NO: 16:

Asp Leu Leu Lys Asn Gly Glu Arg Ile Glu Lys Val Glu Gly Gly Gly
5               10                  15

Ser Ser Gly Ser Ser Ile Glu Phe Ala Arg Leu
20                  25

(2) INFORMATION FOR SEQ ID NO: 17:

(i) SEQUENCE CHARACTERISTICS:
        (A) LENGTH:26 amino acids
        (B) TYPE:amino acids
        (C) TOPOLOGY:linear (ii) MOLECULE TYPE:

(iii) HYPOTHETICAL:

(vi) ORIGINAL SOURCE:
        (A) ORGANISM:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:17:

Asn Gly Gln Glu Glu Lys Ala Gly Val Val Ser Thr Gly Leu Ile Gly
5               10                  15

Gly Gly Ser Ser Ile Glu Phe Ala Arg Leu
20                  25

(2) INFORMATION FOR SEQ ID NO: 18:

(i) SEQUENCE CHARACTERISTICS:
        (A) LENGTH:23 amino acids
        (B) TYPE:amino acids
        (C) TOPOLOGY:linear (ii) MOLECULE TYPE:

(iii) HYPOTHETICAL:

(vi) ORIGINAL SOURCE:

```
            (A) ORGANISM:

(ix) FEATURE:
          (A) NAME/KEY:
          (B) LOCATION:
          (C) IDENTIFICATION METHOD:

(xi) SEQUENCE DESCRIPTION:SEQ ID NO: 18:

Leu His Gly Pro Glu Ile Leu Asp Val Pro Ser Thr Gly Gly Ser
5                   10                  15

Ser Ile Glu Phe Ala Arg Leu
20

(2) INFORMATION FOR SEQ ID NO: 19:

(i) SEQUENCE CHARACTERISTICS:
          (A) LENGTH:13 amino acids
          (B) TYPE:amino acids
          (C) TOPOLOGY:linear (ii) MOLECULE TYPE:

(iii) HYPOTHETICAL:

(vi) ORIGINAL SOURCE:
          (A) ORGANISM:

(ix) FEATURE:
          (A) NAME/KEY:
          (B) LOCATION:
          (C) IDENTIFICATION METHOD:
          (D) OTHER INFORMATION:

(xi) SEQUENCE DESCRIPTION:SEQ ID NO:19:

Asp Leu Leu Lys Asn Gly Glu Arg Ile Glu Lys Val Glu
5                   10

(2) INFORMATION FOR SEQ ID NO: 20:

(i) SEQUENCE CHARACTERISTICS:
          (A) LENGTH:15 amino acids
          (B) TYPE:amino acids
          (C) TOPOLOGY:linear (ii) MOLECULE TYPE:

(iii) HYPOTHETICAL:

(vi) ORIGINAL SOURCE:
          (A) ORGANISM:

(ix) FEATURE:
          (A) NAME/KEY:
          (B) LOCATION:
          (C) IDENTIFICATION METHOD:

(xi) SEQUENCE DESCRIPTION:SEQ ID NO: 20:

Asn Gly Gln Glu Glu Lys Ala Gly Val Val Ser Thr Gly Leu Ile
5                   10                  15

(2) INFORMATION FOR SEQ ID NO: 21:

(i) SEQUENCE CHARACTERISTICS:
          (A) LENGTH:11 amino acids
          (B) TYPE:amino acids
          (C) TOPOLOGY:linear (ii) MOLECULE TYPE:

(iii) HYPOTHETICAL:

(vi) ORIGINAL SOURCE:
```

-continued

```
    (A) ORGANISM:

(ix) FEATURE:
        (A) NAME/KEY:
        (B) LOCATION:
        (C) IDENTIFICATION METHOD:

(xi) SEQUENCE DESCRIPTION:SEQ ID NO: 21:

Thr Ser Ser Ile Glu Phe Ala Arg Leu Glu Phe
5                                       10
```

IMMUNOGENIC CONJUGATED POLYPEPTIDE FOR TREATMENT OF HERPES SIMPLEX VIRUS

This application claims the benefit of Provisional Application No. 60/060,422, filed Sep. 30, 1997.

FIELD OF THE INVENTION

This invention relates to peptide conjugates which can be used to form an immunogenic composition useful to activate the immune system of a patient exposed to or at risk of infection by Herpes Simplex Virus (HSV). More particularly, this invention relates to immunogenic conjugated peptides which contain both a herpes simplex virus specific peptide and an immunomodulatory peptide covalently linked directly or via a linking group and to compositions and diagnostic products containing and methods using such peptide conjugates in the treatment, prevention, or diagnosis of herpes simplex virus.

BACKGROUND OF THE INVENTION

Herpes simplex virus type 1 (HSV-1) and its close cousin, herpes simplex virus type 2 (HSV-2), cause various benign diseases, such as the common cold sore found near the lips and also genital herpes. Herpes simplex virus can also cause serious disease upon infection of the eye (e.g., keratoconjunctivitis, with the potential to lead to blindness), the brain (e.g., encephalitis). Individuals who are immunosuppressed, such as a newborn baby, AIDS patient or transplant patient, are especially vulnerable. HSV infections of immunocompromised individuals and neonates can lead to disseminated and life-threatening disease. Unlike many viruses, once an individual is infected with HSV, the virus remains latent in neurons and can be reactivated by stress or immunosuppression and cause recurrent disease.

A herpes simplex virus vaccine has the potential for use as both a prophylactic to prevent initial infection as well as a treatment to prevent or ameliorate recurrent disease. No vaccine is currently available for prevention or treatment of HSV. Live vaccine development has been hampered because HSV has the capacity to establish latent infection and potentially, to promote neoplastic transformation of cells. The efficacy of live attenuated killed and subunit vaccines has been questioned due to difficulties in eliciting protective cell mediated immune responses.

Cellular immunity and specifically, cytotoxic T lymphocyte cell (CTL) and delayed type hypersensitivity (DTH) responses, are important for the control of HSV. These responses are included in the TH1-type of immune response initiated by CD4 and CD8 T cells following appropriate activation. CD 8 T cells recognize 8–9 amino acid peptides presented by an MHC I molecule and become the target for CTL killing of infected cells. However, immunization with these and other CTL epitope-containing peptides rarely elicits protective immunity because the peptides are too small to be recognized and presented to the immune system. In order to use such a peptide as a vaccine, the peptide must be modified or presented in a manner which will make it more visible to the immune system. Ideally, the modification or manner of presentation should itself be invisible to the immune response and should facilitate the development of the appropriate T cell and overall immune response to the peptide.

T cell responses can be classified by the cytokine profile produced in response to activation. T1 (TH1:CD4 T cells and TC1:CD8 T cells) responses are associated with production of interferon gamma, interleukin-2, lymphotoxin alpha, preferential stimulation of IgG2a production in the mouse, and induction of DTH reactions. T2 (TH2 and TC2) responses are associated with production of interleukin-4, interleukin-10, preferential stimulation of humoral responses, IgG1 production and inhibition of T1 responses. Stimulation of a T2 response may exacerbate infectious diseases which are controlled by protective T1 responses.

Traditionally, small peptides must be attached to carrier proteins in order to elicit immune responses. Often a large protein such as KLH is used. However, it has been observed that heterogenous (impure) KLH yields a better immune response than a more homogenous preparation. Nevertheless, these conjugates tend to promote the production of T2 associated responses and antibody is developed to both the peptide and the carrier.

It would be desirable to find other methods to direct the response primarily or substantially to murine IgG2a or human IgG3, a TH1 associated pathway. It has previously been proposed by one of the present inventors that the carrier should not be directing the response in an undesired direction and since the KLH molecule seems to be predominantly directing the response in the TH2 direction it was concluded that another carrier should be considered. Likewise, other factors such as costs, ease of manufacture, and stability need to be taken into account.

Previous serological studies with *M. tuberculosis* peptides conjugated to a T cell binding ligand (TCBL) derived from the β-2-microglobulin protein of the Major Histocompatibility Complex (MHC) Class I (specifically, at amino acid positions aa 38–50, hereinafter referred to as "β-2M 38–50" or, alternatively, as "Peptide J") induced a TH1-like response whereas similar peptide constructs but using a TCBL, such as MHCIIβ2 135–149 (Peptide G) induced a TH2-like response (Zimmerman, et al., Vacc. Res. 5:103–118, 1995).

Generally, incorporation of an antigenic peptide into a conjugated polypeptide with the appropriate T cell ligand will elicit a defined T cell response. The T cell binding ligand incorporated into the construct will determine whether the response is a TH1 or a TH2 response or mixed or predominantly one or the other of these responses. For any particular disease causing microorganism either or both types of responses may be desirable or preferred. However, elicitation of a TH1 (DTH) type response would be expected to be especially useful against infectious agents which are normally successfully resolved by TH1 (e.g., DTH) responses rather than TH2 responses, associated with mature antibody responses. The conjugated polypeptide technology is effective in allowing small peptides to elicit appropriate TH1 responses (or/and TH2 responses, in appropriate cases) without large protein carriers.

One of the present inventors previously reported that addition of a T cell binding ligand to a peptide epitope could alter the nature of the immune response (i.e., TH1 or TH2). Antibodies derived from certain conjugated polypeptides were better able to recognize the native molecule than were the antibodies prepared by using a conventional peptide-KLH conjugate.

It was shown that the antibodies induced by the heteroconjugate had a broader specificity, so that they recognized the peptide epitope not only in the linear form, but also in the native molecule. In some cases the use of the peptide conjugated to KLH was not able to recognize the epitope in the native molecule. Accordingly, it would be highly desirable to provide a vaccine for HSV which would be effective to prevent initial infection as well as a treatment for individuals who suffer from frequent recurrent disease associated with HSV.

SUMMARY OF THE INVENTION

The present invention relates to certain conjugated polypeptides comprising at least two T cell specific binding peptides covalently linked together, wherein the first peptide binds to a specific class or subclass of T cells and elicits a predominantly T1 or T2 type response and a second peptide is an herpes simplex virus specific antigenic peptide, and wherein the polypeptide is capable of eliciting TH1 associated antibodies when administered to a human in need thereof.

The peptide used as T cell specific binding molecule in the conjugated peptides of this invention are peptides which are portions of molecules or analogues of such portions which bind specifically or at least preferentially to specific class or subclass of T cells, such as helper T cells (TH), suppressor T cells (TS), cytotoxic T lymphocytes (CTL), and the like, and which directs the immune system to a predominantly T1 type immune response against the HSV specific antigenic peptide. These conjugated polypeptides offer the advantages previously seen with other conjugated peptides, such as those more generally disclosed by one of the present inventors in U.S. Pat. No. 5,652,342 (referred to therein as "heterofunctional cellular immunological reagent), of inducing broad spectrum antibodies but, additionally providing a desired T1 specificity.

In particular, the invention provides an immunogenic conjugated polypeptide effective as immunogen in a vaccine for treatment or prevention of infection by herpes simplex virus, said polypeptide represented by the formula $P_1$—x—$P_2$ or $P_2$—x—$P_1$ where $P_1$ represents a herpes simplex virus specific antigenic peptide from a herpes simplex virus type 1 or type 2, selected from the group consisting of the ICP27 protein, glycoprotein B, ribonucleotide reductase, ICP4, ICP34.5, glycoprotein E and glycoprotein F; $P_2$ represents an immunodulatory peptide which is a portion of an immunoprotein which promotes binding to a class or subclass of T cells and which direct a predominantly TH1 type immune response to the peptide $P_1$; and x represents a covalent bond or a divalent peptide linking group, which may be cleavable or non-cleavable.

The present invention also relates to pharmaceutically effective compositions containing such conjugated polypeptide for eliciting immunization to infection against Herpes Simplex Virus, HSV, type 1 or type 2, in a human subject. Such compositions, in addition to the conjugated polypeptides of this invention may also, and preferably will, include suitable immunological adjuvant.

Similarly, the invention relates to the use of such conjugated polypeptide and the pharmaceutically effective composition containing same for treating or preventing HSV infection by administering to a human patient in need thereof, a therapeutically or prophylactively effective amount of the conjugated polypeptide as defined above.

The invention also relates to a diagnostic assay for diagnosing the presence of infection (active or latent) in an individual by HSV wherein T cells from the individual to be diagnosed is mixed with the conjugated polypeptide to the above formula $P_1$—x—$P_2$ or $P_2$—x—$P_1$, and thereafter detecting a reaction between previously HSV primmed T cells and conjugated polypeptide. The conjugated polypeptide may be labelled to facilitate detection of the reaction.

The invention will now be described in further detail by way of the following explanations and preferred embodiments and with the aid of the accompanying drawings.

It is expected that HSV immune T cells would behave in differently or otherwise be different in the presence of the conjugated polypeptide compared to niave or non-immune T cells.

DETAILED DESCRIPTION OF THE INVENTION AND PREFERRED EMBODIMENTS

Figure 1:
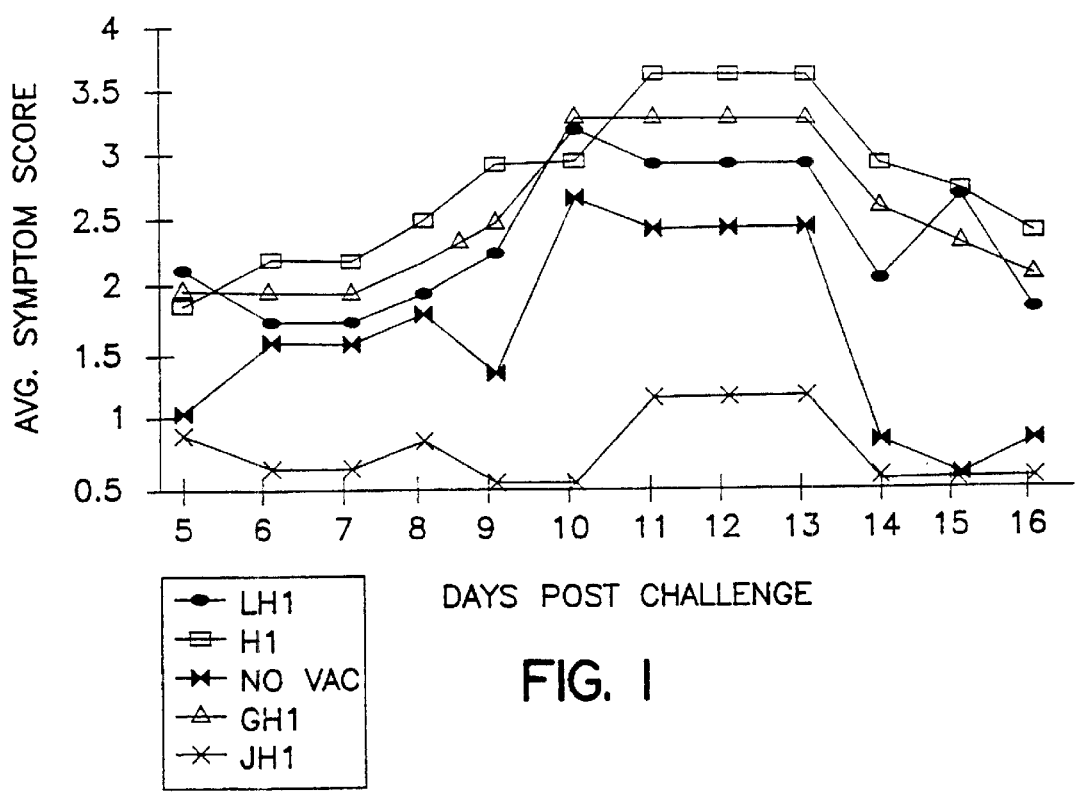
FIG. 1 is a graph plotting the results of Symptomatic Conditions after viral challenge (average symptomatic score versus days post challenge) of non-vaccinated and vaccinated mice (using conjugated polypeptides based on antigenic peptide from ICP27 of HSV-1 or antigenic peptide alone) after intraperitoneal challenge with HSV-1.

For the peptides disclosed above and below and as employed in the experimentation described herein, the amino acid sequences thereof, are set forth by the single identification letter or three-letter identification symbol as follows:

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

-continued

| Amino Acid | Three-letter abbreviation | One-letter symbol |
|---|---|---|
| Tyrosine | Tyr | Y |
| Valine | Val | V |

It should be understood that in any of the amino acid sequences specified herein variations of specific amino acids which do not adversely effect the desired biological activity are contemplated and fall within the scope of the invention. Although the regions of interest of the preferred antigenic peptides are highly conserved, natural and spontaneously occurring amino acid variations are specifically contemplated. In some cases, it may be advantageous to use mixtures of peptides, the sequences of which, within the guidelines given above, and discussed in more detail below, correspond to two or more natural and spontaneously occurring variants of HSV.

Still further, as well recognized in the art, it is often advantageous to make specific amino acid substitutions in order, for example, to provide specific binding sites or for purpose of introducing radioactive or radiisotope or fluorescent tagging of the peptide. Tagging with other types of identifying labels, as well known in the art, such as, for example, toxins and drugs, may also advantageously be included in or with the conjugated peptides of this invention. Such "designed" amino acid sequences are also within the scope of the antigenic peptides of this invention.

In addition, it is also recognized that the amino acids at the N-terminal and C-terminal may be present as the free acid (amino or carboxyl groups) or as the salts, esters, ethers, or amides thereof. In particular amide end groups at the C-terminal and acetylation, e.g., myristyl, etc. at the N- or C-terminal, are often useful without effecting the immunological properties of the peptide.

The peptides $P_1$ and $P_2$ (as hereinafter defined) of the conjugated polypeptides of the present invention can be prepared by conventional processes for synthesizing proteins, such as, for example, solid phase peptide synthesis, as described by Merrifield, R. B., 1963, J. of Am. Chem. Soc., 85:2149–2154. It is also within the scope of the invention and within the skill in the art to produce the novel conjugated peptides of this invention or the peptide components thereof by genetic engineering technology.

The conjugated polypeptides of this invention may be represented by the formula

 (I)

or

 (II).

In the above formulas, $P_1$ represents an herpes simplex virus specific antigenic peptide from a herpes simplex viral protein. The antigenic peptide is preferably one selected from one of the following herpes simplex viral proteins ICP27, glycoprotein B, ribonucleotide reductase, ICP4, ICP34.5, glycoprotein E and glycoprotein F. The ICP27 protein of herpes simplex virus type 1 or type 2, and glycoprotein B (gB) of herpes simplex virus type 1 are especially preferred.

$P_2$ represents an immunomodulatory peptide which is a portion of an immunoprotein which promotes binding to a class or subclass of T cells and which will direct a predominantly TH1 type immune response to the peptide $P_1$.

x represents a covalent bond or a cleavable or non-cleavable divalent peptide linking group.

Preferred antigenic peptides $P_1$ include a peptide comprising amino acid residues 322 to 332 (LYRTFAGNPRA) (SEQ ID NO:1) (hereinafter may be referred to as Peptide H1) of the ICP27 protein of herpes simplex virus type 1 (HSV-1), a peptide comprising amino acid residues AEIDYATLGVGV (SEQ ID NO:2) (hereinafter may be referred to as Peptide H2) of the ICP27 protein of HSV-1; a peptide comprising amino acid residues 448 to 456 (DYATLGVGV) (SEQ ID NO: 3) of the ICP27 protein of HSV-1; a peptide comprising amino acid residues 498 to 505 (SSIEFARL) (SEQ ID NO:4) (hereinafter may be referred to as Peptide B1) from glycoprotein B of HSV-1, a peptide comprising amino acid residues 128 to 139 (DRRDPLARYGSR) (SEQ ID NO:5) from glycoprotein C of HSV-1.

In addition, a peptide comprising from about 10 to about 30 consecutive amino acid residues taken from residues 1 to 30 of SEQ ID NO:6, such as, for example, residues 9 to 21 (LKMADPNRFRGKD) (SEQ ID NO:7), residues 8 to 23 (SLKMADPRNRFRGKDLP) (SEQ ID NO: 8) or amino acid residues 1 to 30 (KRALADASLKMADPNRFRGKD LPVLDQLTD) (SEQ ID NO: 6) from glycoprotein D of HSV-2 (see Bosch, et al., J. Virol. 61:3607, 1987); Weijer, et al., J. Virol. 62:501, 1988), may also be effectively used as the peptide $P_1$.

The HSV specific antigenic peptide may be chosen from any of the HSV type 1 or type 2 proteins which has been found to elicit a protective T cell response. Of particular interest is the ICP27 protein, found in both type 1 and type 2.

ICP27 is an early, nuclear protein of HSV which elicits a protective T cell response but does not elicit a protective antibody response. Rouse, et al. have shown that up to 25% of the T cell response is directed toward ICP27 during natural infection. The ICP27 protein elicits predominantly a TH1 response (Manickan E, et al. and Rouse B. 1995, J. Virol. 69:4711–4716). As a nuclear protein of HSV, the ICP27 protein is also advantageous in that it should not be under immunological selection to undergo mutation. In particular, the aa 322–332 peptide is recognized by cytotoxic T cells from Balb/c mice (H2d major histocompatibility group). (Banks, et al., J. Virol. 67:613–616, 1993). As a nuclear antigen, the ICP27 protein and its peptides will not elicit a protective antibody response.

However, the ICP27 aa 322–332 peptide (H1) is insufficient in and of itself to induce an immune response.

The ICP27 protein peptide at amino acid residues aa 448 to 456 was also identified by these authors, e.g., Rouse, et al. as CTL peptide containing a T cell epitope, and can be used as peptide $P_1$.

Another HSV specific antigenic peptide of interest is the peptide at aa 498 to 505 of glycoprotein B (gB) from HSV-1. This peptide has been identified as a cytotoxic T cell lymphocyte (CTL) target by testing a library of nested, overlapping synthetic peptides for conversion of uninfected cells into target cells (Hanke, et al., J. Virol. 65:1177–1186, 1991). Cells were incubated with the peptides and then challenged with CTLs present in mice immunized by infection with HSV-1.

The peptide 498–505 has the following sequence (SEQ ID NO:4)

Ser Ser Ile Glu Phe Ala Arg Leu.

A longer peptide 497–507 which is also immunogenic but less potent may also be used:

Thr Ser Ser Ile Glu Phe Ala Arg Leu Glu Phe     (SEQ ID NO:8)

The gB peptides differ from the ICP27 peptides in that the former peptide elicits immunological response in H-2K$^b$ mice (e.g., C57Bl/6) whereas the latter elicits a response in Balb-C mice.

More generally, peptides from the glycoproteins gB and gD as described in the literature, e.g., Koelle, et al., J. Virol. 68:2803–2810, 1994; Cose, et al., J. Virol. 69:5844–5852, 1995; Heiligenhause, et al., Eye, 9:89–95, 1995; Damhof, et al., Arch. Virol. 130:187–193, 1993; Wachsman, et al., Vaccine, 10:447–454, 1992, the disclosures of which are incorporated herein in their entireties, may elicit CTL and protective response. Even where such T cell epitope-containing peptides, $P_1$, do not elicit protective antibody response, the antibodies which are produced should be able to bind to virion and infected cell surfaces and, therefore, would be useful in the conjugated polypeptides of this invention not only for therapeutic and immunological activity but also for immunological diagnostic assays.

In the present invention, the antigenic peptide $P_1$ is conjugated to a T cell binding peptide $P_2$. Any T cell binding peptide which is associated with predominantly a TH1 type immune response may be used as peptide $P_2$ in this invention. More particularly, peptide $P_2$ is preferably chosen from the portion of an immunoprotein which promotes its binding to T-cells. A preferred example is peptide J from β-2-microglobulin (β-2M 35–50) (Parham, et al., 1983, J Biol Chem. 258:6179; Zimmerman, et al.) Other related β-2M peptides include amino acid residues 24 to 58 and amino acid residues 58 to 84, as described more fully in U.S. Pat. No. 5,652,342. Examples of other peptides which may be used as peptide $P_2$ of the conjugated polypeptides of the invention may be found in commonly assigned U.S. Pat. No. 5,652,342, the disclosure of which is incorporated herein in its entirety by reference thereto. Guidelines for selection of these or other suitable T cell binding peptides are discussed therein as well as in the Zimmerman, et al. article. Mention may be made of, for example, the molecules known as B7 (Freeman, et al., Science 262:909); B70 (Azuma, et al., 1993, Nature 366:76); GL1 (Hathcock, et al., 1993, Science 262:905); CD58 (Arulanandam, et al., 1993, Proc. Nat. Acad. Sci. 90:11613), CD40 (van Essen, et al., 1995, Nature 378:620); and ICAM-1 (Becker, et al., 1993, J. Immunol. 151:7224). Other potentially useful immunogenic peptides as $P_2$ include, for example, MHC class 1α3 domain comprising a.a. residues 223–229 or 223–230 (Peptide E, Salter, et al., Nature, 345:41, 1990); Interleukin Iβ, residues 163–171 (Nenconi, et al., J. Immunol. 139:800, 1987); MHC class II β2 domain, a.a. 135–149 (Konig, et al., Nature 356:796, 1992); Cammarota, et al., Nature 356:799, 1992). The reader is referred to these literature articles for further details.

Conjugated polypeptides according to the invention may be prepared by directly bonding an antigenic specific peptide $P_1$ to a T cell binding peptide $P_2$ or by bonding the peptides $P_1$ and $P_2$ via a linking group, by conventional techniques, or as more particularly described in detail in the aforementioned U.S. Pat. No. 5,652,342, the disclosure of which is incorporated herein in its entirety by reference thereto. When x represents the divalent linking group, it may be comprised of one or more amino acids, such as, for example, glycine-glycine, or a bifunctional chemical linking group, such as, for example, N-succinimidyl-3-(2-pyridyldithio) propionate (SPDP), m-maleimidobenzoyl-N-hydroxy-succimide ester (MBS), 1-ethyl-3-(3-dimethylaminopropyl) carbodiimide (EDC), or any other reagent commonly employed to link peptides. Again, reference is made to the disclosure of U.S. Pat. No. 5,652,342 for further details.

The linking group will generally be non-cleavable under the conditions of use, however, cleavable groups may also be used where it is desired to separate peptide $P_1$ or peptide $P_2$ after the conjugated peptide bonds to its target T cell. For example, the linking group x may be one which is enymatically cleavable or cleavage may be induced, such as by photoactivation, including for example, exposure to UV radiation.

The immunogenic conjugated peptides of this invention can elicit an immune response to HSV (as shown in the examples to follow) that can be directed toward the desired TH1 as evidenced by the numerous examples of the TH1 characteristic antibody IgG2a (mouse) or IgG3 (man), and/or by a DTH response.

The order of the antigenic peptide $P_1$ and T cell binding peptide $P_2$ is not usually critical and may be reversed. For example, if first peptide=$P_1$ and second peptide=$P_2$ then the conjugated peptide may have the sequence $P_1$—x—$P_2$ or $P_2$—x—$P_1$ Also, while the peptide $P_1$ and peptide $P_2$ may be directly coupled to each other, (i.e., x is a direct peptide bond) in some cases a small linker sequence or a larger heterolinker molecule may be advantageously used to couple the two peptides. For example, as the spacer, one or a few, up to about 5, preferably, up to about 3, neutral amino acids, such as glycine, may be used to link the peptides. A preferred spacer peptide is GGG, however, the spacer may be made larger or smaller and altered to include other molecules besides the amino acid glycine. As examples of heterolinkers mention may be made of, for example, N-succinimidyl-3-(2-pyridylthio)propinate (SPDP), m-maleimidobenzoyl-N-hydroxy-succimide (MBS) as well as any of the other reagents employed to link peptides, including without limitation those disclosed in the aforementioned U.S. Pat. No. 5,652,342. When the peptides P1 and P2 are not directly bonded the linking group will generally and preferably be any divalent linking group. The linking group may be cleavable or non-cleavable under physiological conditions or by appropriate inducement.

Although the total number of amino acids in the conjugated polypeptide is not particularly critical, from a practical aspect, the minimum number of amino acids, including any amino acid spacers or linkers, will generally be at least about 15 or 16, preferably at least about 20, to obtain adequate antigen presentation and immunogenicity. Moreover, from practical considerations of ease of manufacture by synthetic techniques, the maximum number of amino acids will often be less than about 100, preferably, no more than about 70, especially, no more than about 50. However, where the conjugated polypeptide may be manufactured by genetic engineering techniques, much larger molecules may be useful.

The conjugated polypeptide of this invention, e.g., Peptide J (β-2M, 38–50) as $P_1$ and the peptide H1 as $P_2$, may be used to direct the immune response as a prophylactic vaccine for a TH1 directed immune response to prevent the infection by HSV, or to direct the immune response as a therapeutic vaccine for a TH1 directed immune response in HSV infected persons perhaps in conjunction with other therapies, to reduce viral load and to control or cure the infection by HSV. The conjugated polypeptides may also be used to direct the immune response as a prophylactic vaccine to induce a TH1, TH2 or mixed TH1/TH2 directed immune response to prevent the infection by HSV, or to direct the immune response as a therapeutic vaccine to induce a TH1, TH2 or mixed TH1/TH2 directed immune response against the HSV virus, perhaps in conjunction with other therapies to reduce the viral load and to control or cure the infection by HSV.

The conjugated polypeptides of this invention may be used as a vaccine either prophylactically or therapeutically. When provided prophylactically the vaccine is provided in advance of any evidence of HSV. The prophylactic administration of the invention vaccine should serve to prevent or attenuate HSV disease in a mammal. In a preferred embodiment a human, at high risk for HSV is prophylactically treated with a vaccine of this invention. When provided therapeutically, the vaccine is provided to enhance the patient's own immune response to the HSV antigen and, hence, control of disease.

While it is possible for the immunogenic conjugated polypeptide to be administered in a pure or substantially pure form, it is preferable to present it as a pharmaceutical composition, formulation or preparation.

The formulations of the present invention, both for clinical and for human use, comprise a conjugated polypeptide as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

In general, the formulations are prepared by uniformly and intimately bringing into association the active ingredient with liquid carriers or finely divided solid carriers or both, and then, if necessary, shaping the product into the desired formulation.

Formulations suitable for any route of administration may be used, such as, for example, intravenous, intramuscular, subcutaneous, intraperitoneal, nasal, oral, rectal, vaginal, etc. Generally, the formulations will comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer. Illustrative stabilizers include polyethylene glycol, proteins, saccharides, amino acids, inorganic acids, and organic acids which may be used either on their own or as admixtures. These stabilizers, when used, are preferably incorporated in an amount of about 0.1 to about 10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of about 0.1 to about 3.0 osmoles, preferably in the range of about 0.3 to about 1.2. The pH of the aqueous solution is adjusted to be within the range of about 5.0 to about 9.0, preferably within the range of 6–8. In formulating the immunogen of the present invention, antiadsorption agent may be used.

Additional pharmaceutical methods may be employed to control the duration of action. Controlled release preparations may be achieved through the use of polymer to complex or absorb the conjugated polypeptide. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the conjugated polypeptide into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacrylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others. These carriers may likewise be used for preparing to be administered via other cavities, e.g., nasal, rectal, etc.

The conjugated polypeptides of the present invention may be supplied in the form of a kit, alone, or in the form of a pharmaceutical composition as described above.

Vaccination can be conducted by conventional methods. For example, the immunogenic polypeptide can be used in a suitable diluent such as saline or water, or complete or incomplete adjuvants. The immunogen can be administered by any route appropriate for antibody production such as intravenous, intraperitoneal, intramuscular, subcutaneous, and the like. The immunogen may be administered once or at periodic intervals until, for example, a significant titer of $CD4^+$ or $CD8^+$ T cell and/or antibodies directed against the HSV antigen is obtained. In particular, the antigenic polypeptides of the invention elicit TH1 associated antibodies and other aspects of a TH1 immune response. The presence of immune cells versus non-immune cells may be assessed in vitro by measuring cytokine secretion, lymphoproliferation, cell activation markers, cytotoxicity, or altered metabolism, in response to T cells pulsed with the immunogen or by DTH using the conjugated polypeptide in vivo. The antibody may be detected in the serum using conventional immunoassays.

As noted above, the administration of the vaccine of the present invention may be for either a prophylactic or therapeutic purpose. When provided prophylactically, the immunogen is provided in advance of any evidence or in advance of any symptom due to HSV, especially in patients at significant risk for occurrence. The prophylactic administration of the immunogen serves to prevent or attenuate disease HSV in a human. When provided therapeutically, the immunogen is provided at (or after) the onset of the disease or at the onset of any symptom of the disease. The therapeutic administration of the immunogen serves to attenuate the disease.

The invention also concerns a method for treating or preventing herpes simplex virus (HSV) by administering to a human patient in need thereof a therapeutically effective amount of the conjugated polypeptide of this invention, such as the polypeptide of formula (I).

According to this invention the immune response is at least predominantly directed toward at least the desired TH1 response as evidenced by the examples of the TH1 characteristic antibody IgG2a (mouse) and presumably thereby IgG3 (man). These peptides may, however, in addition to the TH1 elicited immune response, elicit a TH2 immune response, and in particular, a mixed TH1/TH2 immune response.

The present invention, therefore, provides antigenic conjugated polypeptides, which provide powerful vaccines for eliciting immune response for neutralizing HSV and killing HSV infected cells. Therefore, the vaccines of this invention can be used to immunize patients at risk for HSV or exposed to HSV including HSV-1 and HSV-2.

The conjugated polypeptides, which may be prepared by conventional solid phase peptide synthesis or other conventional means for peptide synthesis, however, the peptides may also be prepared by genetic engineering techniques. The DNA sequences coding for the peptides of this invention can be prepared by any of the well known techniques for recombinant gene technology. For example, reference can be made to the disclosure of recombinant proteins and peptides in U.S. Pat. No. 5,142,024 and the body of literature mentioned therein, the disclosures of which are incorporated herein by reference thereto.

Thus, this invention also provides a recombinant DNA molecule comprising all or part of the nucleic acid sequence encoding the antigenic peptide or the immunomodulatory peptide for subsequent direct linking or linking via a linking group, as previously described, or, more preferably, encoding the conjugated polypeptide of formula $P_1$—x—$P_2$ or $P_2$—x—$P_1$, as described above, and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (see, e.g., Ausubel, et al., (1987) in "Current Protocols in Molecular Biology", John Wiley and Sons, New York, N.Y.) or are commercially available.

Another aspect of this invention relates to a host organism into which a recombinant expression vector containing all or part of the nucleic acid sequence encoding for the immunogenic conjugated polypeptide as described above, has been inserted. The host cells transformed with the nucleic acid sequences encompassed by this invention include eukaryotes, such as animal, plant, insect and yeast cells and prokaryotes, such as $E.\ coli$. The means by which the vector carrying the gene may be introduced into the cell include, but are not limited to, microinjection, electroporation, transduction, or transfection using DEAE-dextran, lipofection, calcium phosphate or other procedures known to one skilled in the art (see, e.g., Sambrook, et al. (1989) in "Molecular Cloning. A Laboratory Manual", Cold Spring Harbor Press, Plainview, N.Y.).

In a preferred embodiment, eukaryotic expression vectors that function in eukaryotic cells are used. Examples of such vectors include, but are not limited to, retroviral vectors, vaccinia virus vectors, adenovirus vectors, herpes virus vector, fowl pox virus vector, plasmids, such as pCDNA3 (Invitrogen, San Diego, Calif.) or the baculovirus transfer vectors. Preferred eukaryotic cell lines include, but are not limited to, COS cells, CHO cells, HeLa cells, NIH/3T3 cells, 293 cells (ATCC#CRL1573), T2 cells, dendritic cells, monocytes or Epstein-Barr Virus transformed B cells. Mammalian cells, such as NIH/3T3, COS-7, CHO, 293 cells. (ATCC #CRL 1573), T2 cells, dendritic cells, or monocytes are generally preferred to ensure proper processing and modification of the protein.

The recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (see, e.g., Ausubel, et al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the antigenic peptide (Ausubel, et al., (1987) in "Current Protocols in Molecular Biology" John Wiley and Sons, New York, N.Y.).

By way of example, a vaccine prepared using recombinant expression vectors may be used. To provide a vaccine to an individual a genetic sequence which encodes for all or part of the immunogenic conjugated polypeptide is inserted into an expression vector, as described above, and introduced into the mammal to be immunized. Examples of vectors that may be used in the aforementioned vaccines include, but are not limited to, defective retroviral vectors, andenoviral vectors, vaccinia viral vectors, fowl pox viral vectors, or other viral vectors (Mulligan, R. C., (1993) $Science$ 260:926–932). The viral vectors carrying the nucleic sequence can be introduced into a mammal either prior to any evidence of HSV or to mediate progression of the disease in a mammal afflicted with HSV.

Examples of methods for administering the viral vector into the mammals include, but are not limited to, exposure of cells to the virus ex vivo, or injection of the retrovirus or a producer cell line of the virus into the affected tissue or intravenous administration of the virus. The quantity of viral vector, carrying the appropriate nucleic acid sequence encoding for the immunogenic conjugated polypeptide to be administered is based on the titer of virus particles. By way of example, a range of the immunogen to be administered may be about $10^6$ to about $10^{11}$ virus particles per mammal, preferably a human. After immunization the efficacy of the vaccine can be assessed by production of antibodies or immune cells that recognize the antigen, as assessed by specific cytokine production or by disease regression. One skilled in the art would know the conventional methods to assess the aforementioned parameters, such as CTL lympoproliferation, etc.

Moreover, the conjugated polypeptides of this invention and DNA sequences encoding same may be used in a genetic immunization technique, such as disclosed in U.S. Pat. No.

5,593,972, the disclosure of which is incorporated herein in its entirety by reference thereto. According to the genetic immunization technique, the nucleotide sequence is operatively linked to regulatory sequences to enable expression in cells of an individual to which the nucleic acid molecule is administered. The resulting cells may then be used for prophylactic or therapeutic immunization.

When used as a vaccine in the method of this invention, the vaccine can be introduced into the host most conveniently by injection, intramuscularly, intradermally, parenterally, orally or subcutaneously. Any of the common liquid or solid vehicles may be employed, which are acceptable to the host and which do not have any adverse side effects on the host or any detrimental effects on the vaccine. Phosphate buffered saline (PBS), at physiological pH, e.g. pH 6.8 to 7.4, preferably pH 7, may be used as a carrier, alone or with a suitable adjuvant. The concentration of immunogenic polypeptide may vary from about 0.1 to 200 μg/kg, such as about 25 μg/kg per injection, in a volume of clinical solvent generally from about 0.1 to 1 ml, such as about 0.2 ml, preclinical studies in animals, and from about 0.5 ml to about 2 ml, such as about 1 ml in humans. Multiple injections may be required after the initial injections and may be given at intervals of from about 2 to 4 weeks, for example, about 2 weeks in animals and about 8 weeks in humans, when multiple injections are given.

A preferred concentration of immunogenic polypeptide in the vaccines of the present invention may be in the range of from 10 to 25 μg/kg, however, a higher dose may be administered as needed.

The following are exemplary of applications for various embodiments of the conjugated polypeptides of the invention but, it is understood that the invention is not restricted to the following described examples.

EXAMPLES

I. Peptides

One T cell binding peptide $P_2$ of the conjugated polypeptide used in these studies includes a region of β-2 microglobulin, aa 35–47, Peptide J (shown underlined) and modified to include a spacer, for a MHC Class I-like action PEPTIDE J DLL KNG ERI EKV EGG C-amide (SEQ ID NO:9)

The conjugate with the antigenic peptide $P_1$ and the Peptide J contained a spacer of one additional glycine substituted for the C-terminal cysteine for a total of three glycine residues. Accordingly, the conjugated polypeptide (J-H1) had the following formula DLL KN GER IEK VEG GGL YRT FAG NPR
A                                (SEQ ID NO:10)

wherein the underlined portion represents peptide H1. Similarly polypeptide (J-H2) is prepared with the formula DLL KN GER IEK VEG GGA EID YAT LGV
GV                               (SEQ ID NO:11)

Other representative polypeptides which can be prepared according to this invention or as controls are shown in the following Table 1.

TABLE 1

| | |
|---|---|
| NGQ EEK AGV VST GLI GGG LYR TFA GNP RA (SEQ ID NO:12) | (G-H1) |
| LHG PEI LDV PST GGG LYR TFA GNP RA (SEQ ID NO:13) | (L-H1) |

TABLE 1-continued

| | |
|---|---|
| LHG PEI LDV PST GGG AEI DYA TLG VGY (SEQ ID NO:14) | (L-H2) |
| NGQ EEK AGV VST GLI GGG AEI DYA TLG VGY (SEQ ID NO:15) | (G-H2) |
| DLL KNG ERI EKV EGG GSS IEF ARL (SEQ ID NO:16) | (J-B1) |
| NGQ EEK AGV VST GLI GGG SSI EFA RL (SEQ ID NO:17) | (G-B1) |
| LHG PEI LDV PST GGG SSI EFA RL (SEQ ID NO:18) | (L-B1) |

The peptides may be synthesized using the FMOC procedure and a double coupling protocol for the first 8 residues. Usually the peptide is prepared with the carboxyl terminus as an amide form. The peptides may be purified using preparative HPLC, and analyzed by an analytical HPLC, amino acid analysis and mass spectrophotometer. The peptides should be greater than 95%, usually greater than 98%, pure by HPLC criteria. The dry peptides are stored in glass vials with desiccant at −20° C.

II. Preparation of Conjugated Polypeptides

The conjugated polypeptide may be synthesized as a single peptide without any conjugation step or by conjugation of the peptide $P_1$ and the peptide $P_2$ by using the thioether method or by any other conjugation method known to the skilled practitioner.

Formulations for the following tests are adjusted to contain about 1000 μg/ml of peptide, and stored frozen (−20° C.) in aliquots ready for thawing and may be administered in combination with an adjuvant (e.g., alum, MPL, ICFA, QS21, SF59, SAF-1) and/or carrier (e.g., liposomes or Novasomes). In particular, the peptides may be emulsified in Novasome adjuvants. Other adjuvants, such as, for example, Hunter's TiterMax (CYTRX) may also be used.

III. Immunization, Anti-sera Collection and Processing

An intraperitoneal challenge model using mice test animal was selected although the predominant presentation of HSV disease is not intraperitoneal since a reproducible course of disease occurs following viral challenge; since the viral challenge dose can be well defined and readily delivered by intraperitoneal injection since the symptoms are readily detected and the course of disease can be qualitatively evaluated; and since the relevant parameter of survival may be readily evaluated. Immune function studies may also be conducted in vitro to further characterize the responses to the test vaccines.

Procedure A for Peptide H1 of ICP27

In a series of experiments, groups (12 per group) of 3 week old Balb/c female mice (Taconic Farms, Germantown, N.Y.) are immunized and test bled according to the following schedule. Schedule A: immunizations on day 0 and day 14, and two weeks later nine mice of each group are challenged moderately with a lethal dose (<$LD_{50}$) of HSV (H129 clinical strain) administered intraperitoneally. In this regard, young Balb/c mice show a defined course of disease which progresses from abdominal swelling, lethargy, paraplegia, to death within 1 to 2 weeks. Therefore, the effectiveness of the vaccinations may be readily determined.

The following Table 2 identifies each group with respect to the peptide which was tested.

TABLE 2

Immunization and Challenge Schedule

| Group* cells | Immunization | Challenge | Unchallenged Immune Studies; Blood, DTH and Spleen |
|---|---|---|---|
| A NoVac | 0 | 9 | ** |
| B H1 | 12 | 9 | 3 |
| C G-H1 | 12 | 9 | 3 |
| D L-H1 | 12 | 9 | 3 |
| E J-H1 | 12 | 9 | 3 |

*The group of 12 mice were divided into the two groups as indicated. The dose of peptide was determined on a molar basis using 100 µg of JH1 as the basis (0.033 µmoles/animal)
**Three infected but surviving mice were available for DTH or naturally immunized antisera.

Each immunization consisted of 33 nmoles of conjugated polypeptide or non-conjugated antigenic peptide H1 (equivalent to 100 µg of the JH1 vaccine). The peptide was mixed with the Novasome liposomal adjuvant (50% v/v). The mice were immunized twice with a two week interval between inoculations. After an additional two weeks, most of the mice received an intraperitoneal challenge with the EKN clinical strain of HSV-1. The mice were evaluated daily for symptoms. DTH evaluation was performed 6 weeks after the initial vaccination on 3 mice that did not receive HSV-1 challenge. Blood was obtained from selected mice for ELISA studies prior to immunization and prior to virus challenge. The results are shown in FIG. 1 for symptom (on a daily basis) and in FIG. 2 for survival following vaccination and sub-lethal challenge.

In FIG. 1 symptoms were scored daily as:
1. non-specific mild symptoms
2. mild swelling of the abdomen
3. significant swelling of the abdomen and malaise
4. incapacitation
5. death From FIG. 1 the following conclusions may be drawn:
1. Unvaccinated (NO VAC) mice exhibited mild symptoms until the tenth day after the challenge at which time they suffered significant swelling of the abdomen and malaise. All but one mouse recovered.
2. JH1 vaccinated mice were protected from disease and only two mice showed significant symptoms, one of these mice died.
3. Mice vaccinated with the H1 peptide, GH1 or LH1 conjugated peptides exhibited more severe symptoms throughout the course of infection and death.
4. Vaccination with the H1 peptide, GH1 or LH1 conjugated polypeptide seemed to exacerbate the disease symptoms.

Figure 2:
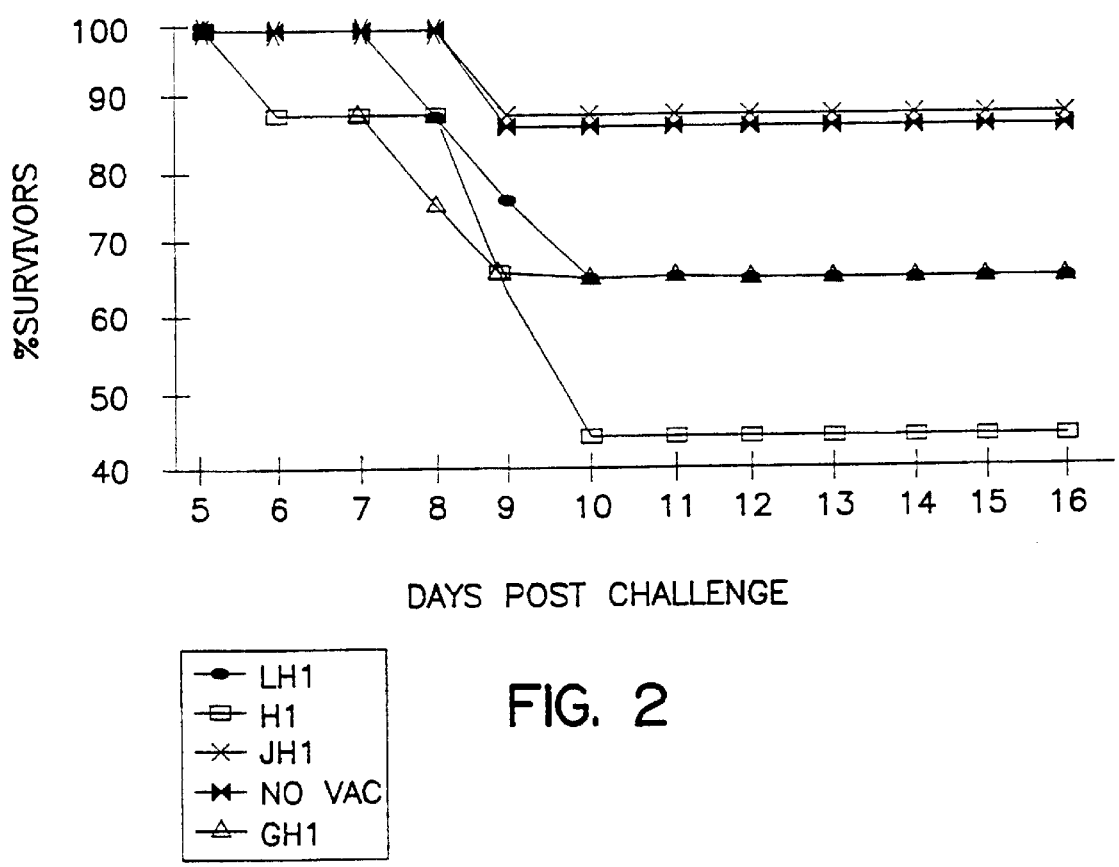
FIG. 2 is a graph plotting the results of survival after viral challenge (% survivors versus days post challenge) of the same vaccinated and non-vaccinated mice as used in the study shown in FIG. 1.

From FIG. 2 it is seen that maximal survival was observed for unvaccinated and JH1 vaccinated mice. Vaccination with the H1 peptide, GH1 or LH1 conjugates seemed to exacerbate the disease symptoms.

Figure 3:
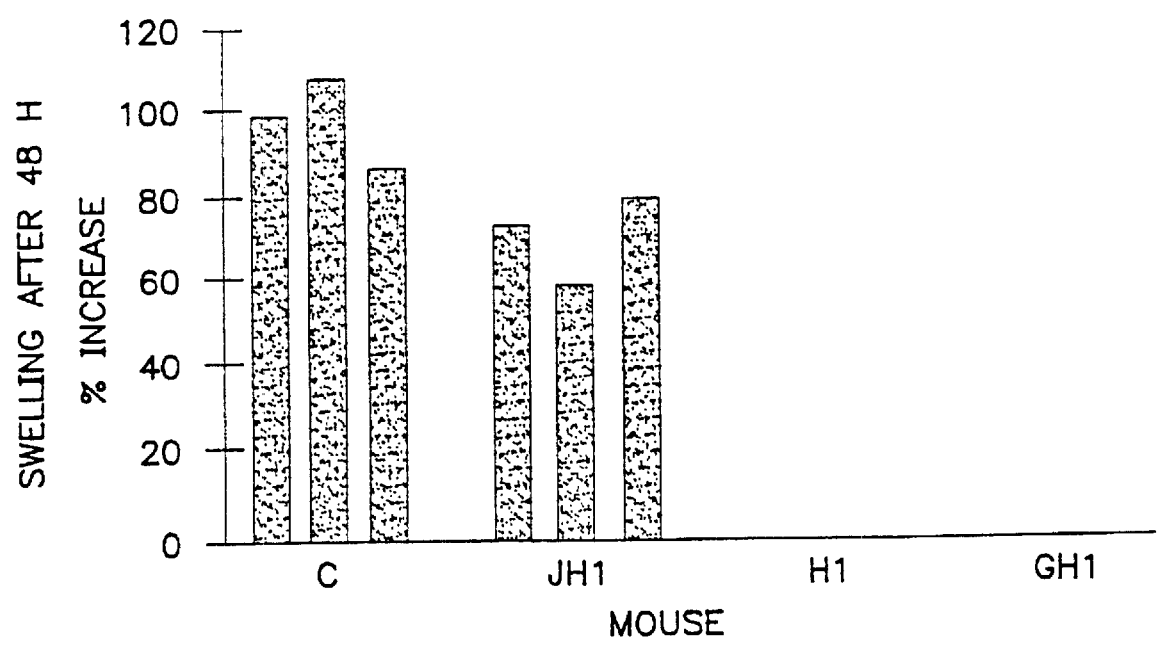
FIG. 3 is a graph plotting the results of Delayed type Hypersensitivity (DTH response as swelling after 48 hours) for three surviving non-vaccinated mice and three each of the vaccinated unchallanged mice as used in the study shown in FIG. 1.

DTH response was evaluated 4 weeks after the last immunization for the vaccinated mice and three unvaccinated HSV challenged mice which had recovered from disease (C). Swelling of the right ear pinna was measured at 48 hours following injection of ultraviolet inactivated HSV and compared to the left ear pinna which had been injected with buffer. The results are shown in FIG. 3.

In another series of parallel experiments Balb/c female mice (n=9) were vaccinated with the H1 peptide or the JH1, GH1 or LH1 conjugated polypeptides according to the same protocol as for the HSV-1 challenge experiment described above. As seen from FIG. 3 DTH was observed qualitatively by redness induced by inflammation and measured quantitatively for the unvaccinated, HSV-1 challenged mice (C) and the JH1 vaccinated mice but not for mice vaccinated with the GH1, LH1 or H1 peptides.

Figure 4:
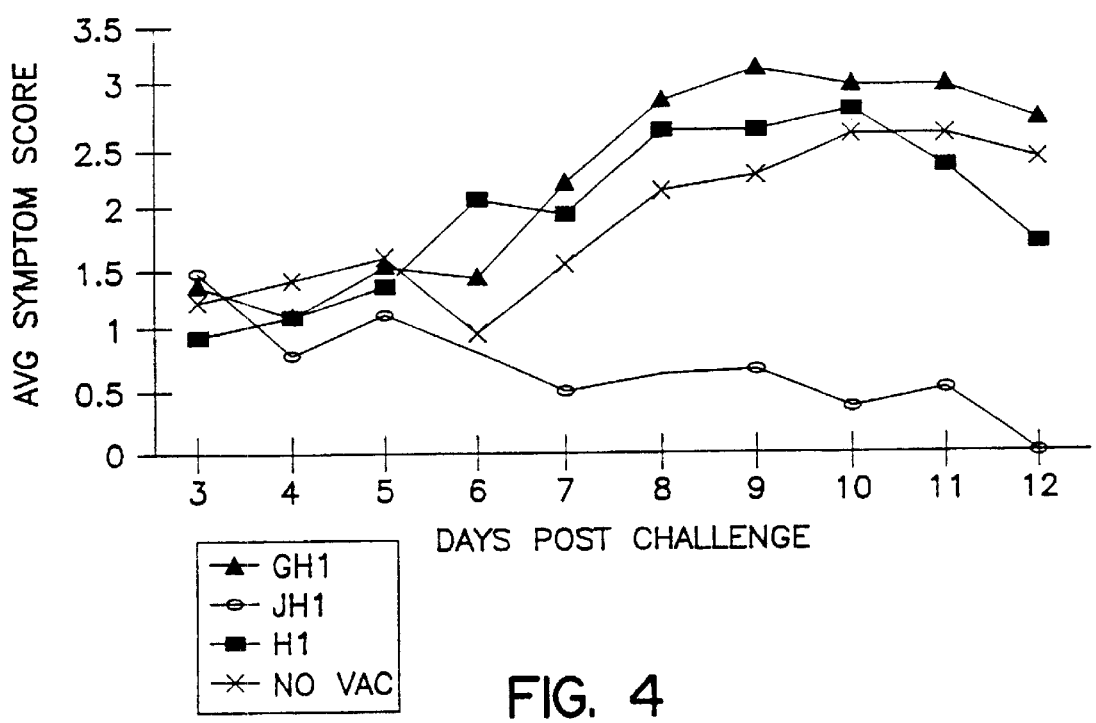
FIG. 4 is a graph similar to FIG. 1 but in a second test procedure following challenge of vaccinated and non-vaccinated mice with an $LD_{50}$ of HSV-1.
Figure 5:
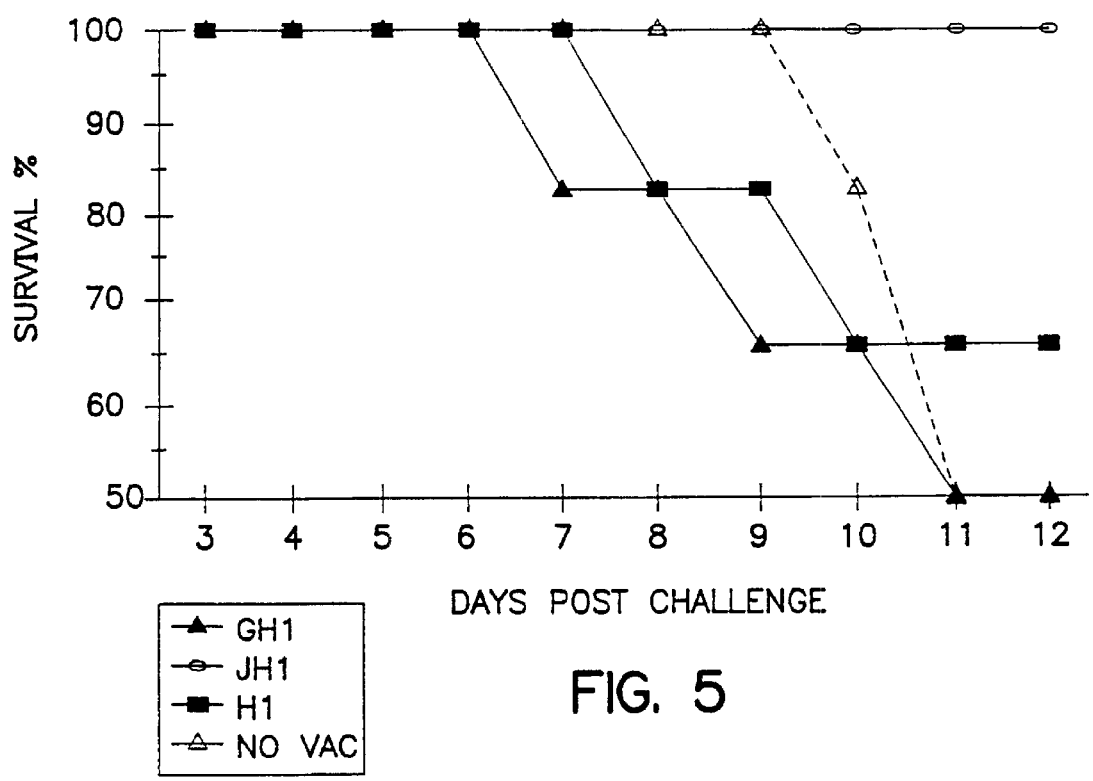
FIG. 5 is a graph similar to FIG. 2 but for the survival of the mice used to prepare FIG. 4.

Similar tests as described above were carried out. Balb/c mice (4 wk old) (n=6) were unvaccinated (NO VAC) or vaccinated and revaccinated two weeks later with the H1 peptide or the indicated conjugated polypeptide. The mice were then challenged two weeks later with an $LD_{50}$ of HSV-1. Symptoms were scored daily as:
1. non-specific mild symptoms
2. mild swelling of the abdomen
3. significant swelling of the abdomen and malaise
4. incapacitation
5. death The results are shown in FIG. 4 for symptoms, in FIG. 5 for survival and in FIG. 6 for DTH.

Unvaccinated mice and mice vaccinated with the H1 peptide, GH1 or LH1 heteroconjugates exhibited severe symptoms and death. However, JH1 vaccinated mice were protected from disease symptoms and death (see FIGS. 4 and 5).

DTH response was evaluated 4 weeks after the last immunization for the vaccinated mice and three unvaccinated HSV challenged mice which had recovered from disease (Ctrl)

The protocol used in this experiment differed slightly from that of FIG. 3. Swelling in the right ear pinna was measured by micrometer prior to and at 24, 48 and 96 hours following injection of ultraviolet inactivated HSV and compared to the left ear pinna which had been injected with an uninfected Vero cell extract. The results are shown in FIG. 6.

Figure 6:
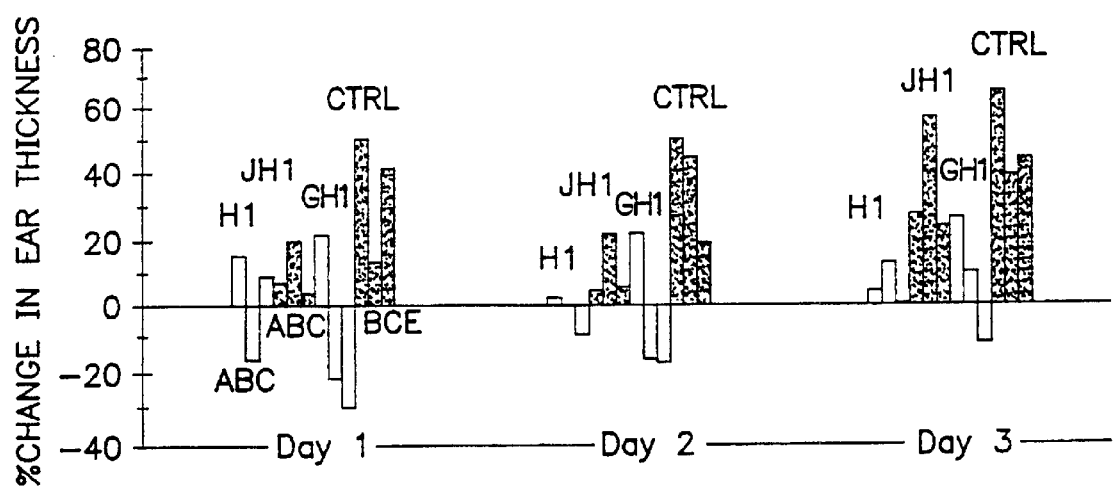
FIG. 6 is a graph of the delayed hypersensitivity response (DTH) as swelling (%) for non-vaccinated and vaccinated mice used to prepare FIG. 4 (using either a conjugated polypeptide or antigenic HSV peptide alone).

From FIG. 6, it is seen that DTH was observed on each day, qualitatively by redness induced by inflammation and quantitatively for all of the mice in the unvaccinated, HSV-1 challenged (C) and the JH1 vaccinated groups. Some swelling but no redness was observed for some but not all of the mice vaccinated with the GH1, LH1 or H1 peptides.

From the above results it is understood that immunization with the conjugated polypeptide wherein a T cell binding peptide elicits predominantly a Th1 type immune response, e.g. Peptide J, provides protection from disease and death following intraperitoneal infection with HSV-1.

Antibody responses to the antigenic peptide, e.g. peptide H1 are undetectable by ELISA.

Mice immunized with the conjugated polypeptide of this invention develop capacity for a DTH response to HSV-1.

Neither the antigenic peptide alone nor the LH1 conjugated polypeptides (the T cell binding peptide L being characterized by eliciting primarily a TH2 type response) nor the GH1 conjugated polypeptide elicited protection and may, in fact, have exacerbated disease and mortality following HSV challenge. These polypeptides did not elicit DTH responses.

Elicitation of protection and DTH responses indicate that immunization with the conjugated polypeptide of the invention stimulates TH1 T cell responses and that T cell responses are sufficient for protection.

These studies, therefore, confirm that covalently binding or conjugating a T cell specific binding peptide which elicits a TH1 type immune response to an antigenic peptide for HSV may enhance and promote the generation of a TH1 type T cell response. These studies are believed to be the first to show that this immune response can be sufficient to elicit protection from infectious challenge.

Procedure B for Peptide B1 of Glycoprotein B

Figure 7:
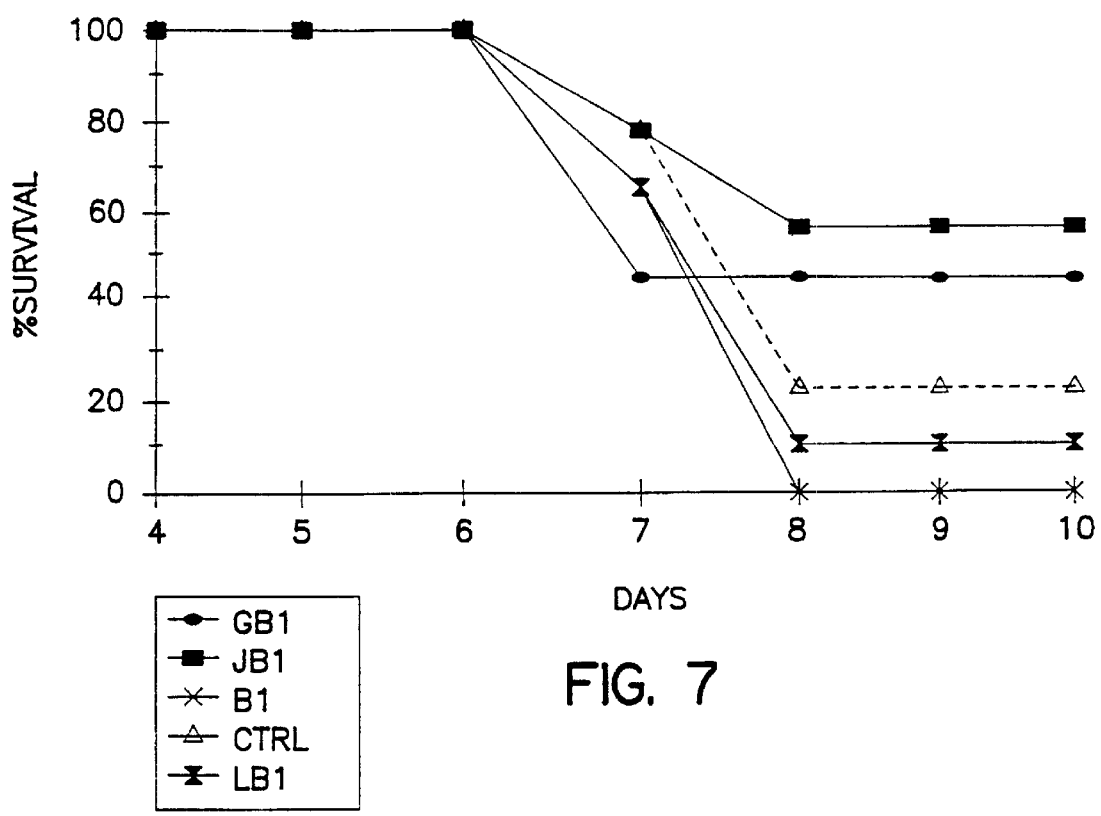
FIG. 7 is a graph of percent survival versus time (days post challenge) for non-vaccinated and vaccinated mice (using conjugated polypeptides based on antigenic peptide from glycoprotein B of HSV-1 or the antigenic peptide alone).

In order to further establish the effectiveness of conjugated peptides according to this invention as effective vaccines for treatment of herpes simplex virus, the HSV epitope B1, which is a T cell epitope (aa 498–505, SSIEFARL) of glycoprotein B found in both HSV-1 or HSV-2 (see Hanke, et al, J. Virol. 65:1177–86; and Bonneau, et al, Virology 195:62–70) was selected and evaluated with either peptide J or peptide G or peptide L as described above. Namely, the conjugated peptides GB1, JB1 and LB1, as described in Table 1 above, were tested under the same conditions as previously described except that in place of the Balb/c mice, C57BI6 mice were vaccinated with the B1 conjugated peptides or non-conjugated B1 peptide (SEQ ID NO:4). The survival results are shown in FIG. 7. The mice immunized with the B1 peptide or with the conjugated peptide LB1 were not protected from HSV-1 challenge (0 of 9 or 1 of 9 survival, respectively, after day 8) and, in fact the B1 and LB1 immunized mice fared worse than the control (unvaccinated) mice (2 of 9 survival after day 8).

In contrast, the mice vaccinated with conjugated peptide GB1 or JB1 had survivals of 55.5% (5 of 9) and 44.4% (4 of 9) respectively, indicative of partial protection.

In DTH tests carried out on 3 unchallenged immunized mice as previously described in connection with FIG. 6, only the mice immunized with the JB1 conjugated peptide vaccine and the HSV challenged, surviving mice exhibited a DTH response. The GB vaccinated mice and the B peptide vaccinated mice did not exhibit a DTH response.

The antibody responses of vaccinated and unchallenged mice, vaccinated and challenged mice and unvaccinated and challenged mice were measured by ELISA assay. Serum was obtained 7 weeks after the initial immunization or 2 weeks after the virus challenge. B1 peptide or infected cell extracts were bound to the ELISA plate as antigen. Results are shown in Table 3 and were taken from pooled serum taken from 2 or 3 mice. The results were corrected for non-specific responses by subtracting the absorbance obtained towards an unrelated antigen.

TABLE 3

ELISA ASSAY OF ANTIBODY RESPONSES
FOLLOWING B1 PEPTIDE VACCINATIONS

| TREATMENT | B1 PEPTIDE RESPONSE | ANTIVIRUS RESPONSE |
|---|---|---|
| B1 Peptide | 0.031 | not tested |
| LB1 polypeptide | 0.031 | not tested |
| GB1 polypeptide | 0.035 | not tested |
| JB1 polypeptide | 0.025 | not tested |
| Normal mouse serum | 0.043 | 0.059 |
| HSV-1 challenged | 0.045 | 0.447 |
| GB1 and challenge | 0.017 | not tested |
| JB1 and challenge | 0.19 | 0.445 |

From the results reported in Table 3 it is seen that no specific antibody was detected following immunization with the conjugated peptide vaccines. Also, no significant difference in response towards whole virus antigen was observed for unimmunized mice.

The large response towards the B1 peptide for mice preimmunized with the JB1 vaccine upon viral challenge is consistent with a prime-boost mechanism of immunization, i.e., antibody production.

When the results of the tests with polypeptides JH1 and GH1 are compared to the results with polypeptides JB1 and GB1, it is presumed that the protection afforded by the GB1 polypeptide compared to the lack of protection with the GH1 polypeptide, whereas both of the Peptide J conjugated polypeptides conferred protection, may be the result of Peptide G eliciting both a B cell (Th2) and a T cell (Th1) response. Similarly, the B1 peptide is believed to exhibit both a CTL epitope and a B cell epitope.

Accordingly, one of ordinary skill in the art will, in view of the above results, be able to determine, based on the nature of the epitopes of the HSV antigenic peptide, the expression of the target cell, and the nature of the response to which the TCBL is directed, the type of protective immunity and, therefore, the most appropriate combinations of the TCBL and the antigenic peptide for forming the conjugated polypeptides of this invention and the vaccines for HSV based thereon.

What is claimed is:

1. An immunogenic conjugated polypeptide effective as immunogen in a vaccine for treatment or prevention of infection by herpes simplex virus, said polypeptide represented by the formula $P_1$-x-$P_2$ or $P_2$-x-$P_1$ where $P_1$ represents a herpes simplex virus specific antigenic peptide from a protein of herpes simplex virus type 1 or type 2, selected from the group consisting of ICP27, glycoprotein B, ribonucleotide reductase, ICP4, ICP34.5, glycoprotein E and glycoprotein F;

$P_2$ represents an immunomodulatory peptide which is a portion of an immunoprotein which promotes binding to a class or subclass of T cells and which direct a predominantly TH1 type immune response to the peptide $P_1$; and x represents a covalent bond or a cleavable or non-cleavable peptide linking group.

2. A conjugated polypeptide according to claim 1 wherein peptide $P_1$ is selected from the group consisting of

| | |
|---|---|
| LYR TFA GNP RA | (SEQ ID NO:1) |
| AEI DYA TLG VGV | (SEQ ID NO:2) |
| DYA TLG VGV | (SEQ ID NO:3) | and

| | |
|---|---|
| SSI EFA RL | (SEQ ID NO:4). |

3. A conjugated polypeptide according to claim 1 wherein peptide $P_2$ is selected from the group consisting of

| | |
|---|---|
| DLL KNG ERI EKV E | (SEQ ID NO:19) | and

| | |
|---|---|
| NGQ EEK AGV VST GLI | (SEQ ID NO:20). |

4. A conjugated polypeptide according to claim 1 which is selected from the group consisting of

| | |
|---|---|
| DLL KNE GER IEK VEG GGL YRT FAG NPR A (J-H1) | (SEQ ID NO:10) |
| DLL KNG ERI EKV EGG GSS IEF ARL (J-B1) | (SEQ ID NO:16) | and

| | |
|---|---|
| NGQ EEK AGV VST GLI GGG SSI EFA RL (G-B1) | (SEQ ID NO:17). |

5. A composition effective in the treatment or prevention of herpes simplex virus comprising a conjugated polypeptide according to claim 1 and a pharmaceutically effective carrier.

6. A method for the treatment or prevention of herpes simplex virus comprising administering to a patient in need thereof a therapeutically effective amount of a conjugated polypeptide according to claim 1.

7. A method for diagnosing the presence of infection active or latent in an individual by herpes simplex virus which comprises mixing T cells from the individual with conjugated polypeptide represented by the formula $P_1$-x-$P_2$ or $P_2$-x-$P_1$ as defined in claim 1 and detecting a reaction between T cells and conjugated peptide.

8. The method of claim 7 wherein the conjugated polypeptide is labelled with a detectable species to facilate detection of said reaction.

* * * * *